United States Patent [19]

Goble

[11] Patent Number: 5,438,302
[45] Date of Patent: Aug. 1, 1995

[54] ELECTROSURGICAL RADIOFREQUENCY GENERATOR HAVING REGULATED VOLTAGE ACROSS SWITCHING DEVICE

[75] Inventor: Colin C. O. Goble, Penarth, Scotland

[73] Assignee: Gyrus Medical Limited, St. Mellons, Wales

[21] Appl. No.: 273,496

[22] Filed: Jul. 11, 1994

[30] Foreign Application Priority Data

Jul. 12, 1993 [GB] United Kingdom ............... 9314391

[51] Int. Cl.⁶ .................... H03B 5/12; A61B 17/36
[52] U.S. Cl. ..................... 331/167; 331/117 FE; 331/173; 606/39
[58] Field of Search ............ 331/65, 74, 77, 112, 331/114, 117 R, 117 FE, 146, 149, 151, 153, 167, 170, 173, 185; 307/269; 363/95-99, 131-134, 40-43, 78; 606/39, 40

[56] References Cited

U.S. PATENT DOCUMENTS

| 2,849,611 | 8/1958 | Adams | 331/170 X |
|---|---|---|---|
| 2,982,881 | 5/1961 | Reich | 331/114 X |
| 3,391,351 | 7/1968 | Trent | 331/114 X |
| 3,571,644 | 3/1971 | Jakoubovitch | 331/151 X |
| 3,743,918 | 7/1973 | Maitre | 315/219 X |
| 4,024,467 | 5/1977 | Andrews et al. | 332/14 |
| 4,145,636 | 3/1979 | Doi | 315/219 X |
| 4,287,557 | 9/1981 | Brehse | 363/95 |
| 4,376,263 | 3/1983 | Pittroff et al. | 320/32 |
| 4,472,661 | 9/1984 | Culver | 315/219 X |
| 4,651,264 | 3/1987 | Shiao-Chung Hu | 331/117 R X |

FOREIGN PATENT DOCUMENTS

| 0325456 | 7/1989 | European Pat. Off. | A61N 1/32 |
|---|---|---|---|
| 2313708 | 12/1976 | France | G05F 1/08 |
| 2164473A | 3/1986 | United Kingdom | A61B 17/36 |
| 2214430A | 9/1989 | United Kingdom | A61N 1/32 |

Primary Examiner—David Mis
Attorney, Agent, or Firm—Fish & Richardson

[57] ABSTRACT

In an electrosurgical generator having a self-tuning oscillator which includes a switching device and a resonant output network connected between the switching device and a supply rail, an oscillator feedback circuit feeds to the switching device a switching control pulse signal for separately switching the switching device to its "on" state whilst the voltage across the device is decreasing, the phase of the "on" point being dynamically variable such that the "on" time of the device is adjusted so as to regulate the amplitude of the voltage thereacross. This allows reverse conduction of the switching device to be avoided, giving improved efficiency.

21 Claims, 3 Drawing Sheets

Output voltage

Primary voltage

Reverse conduction of switching device

90° Phase Advance $I_D$

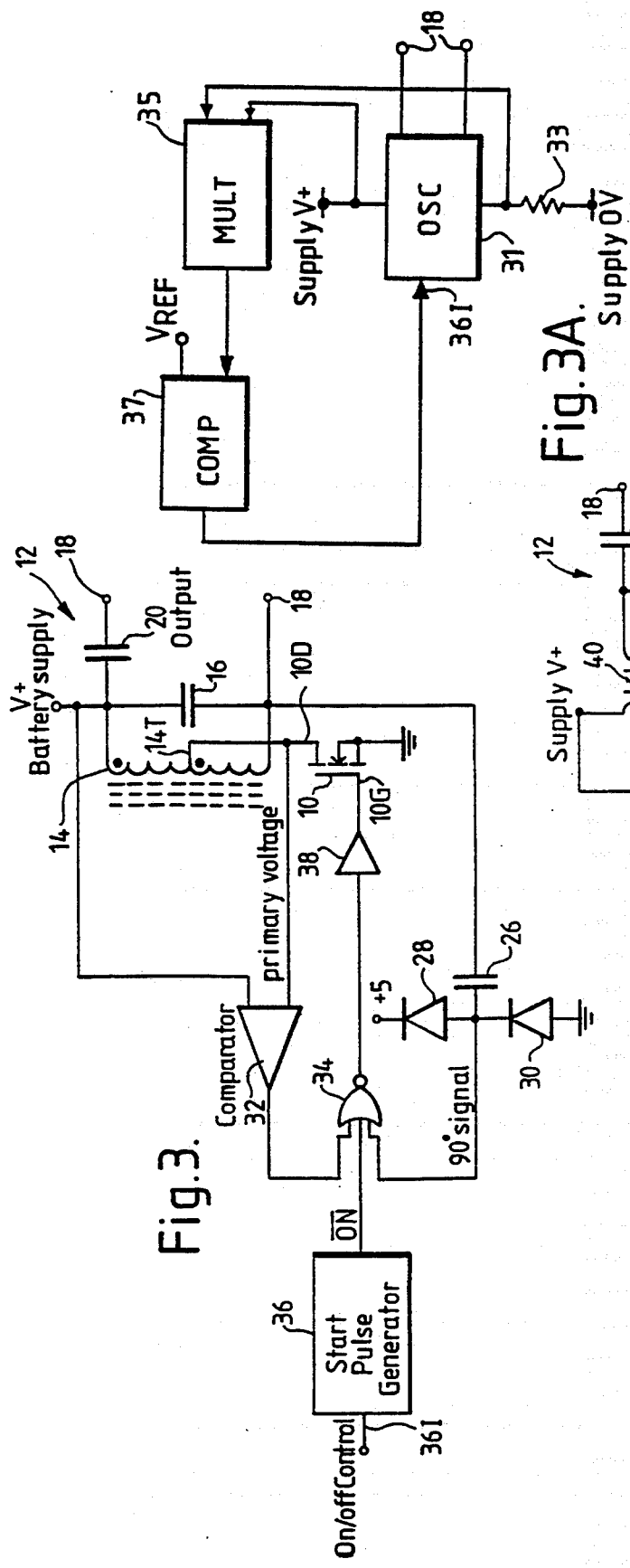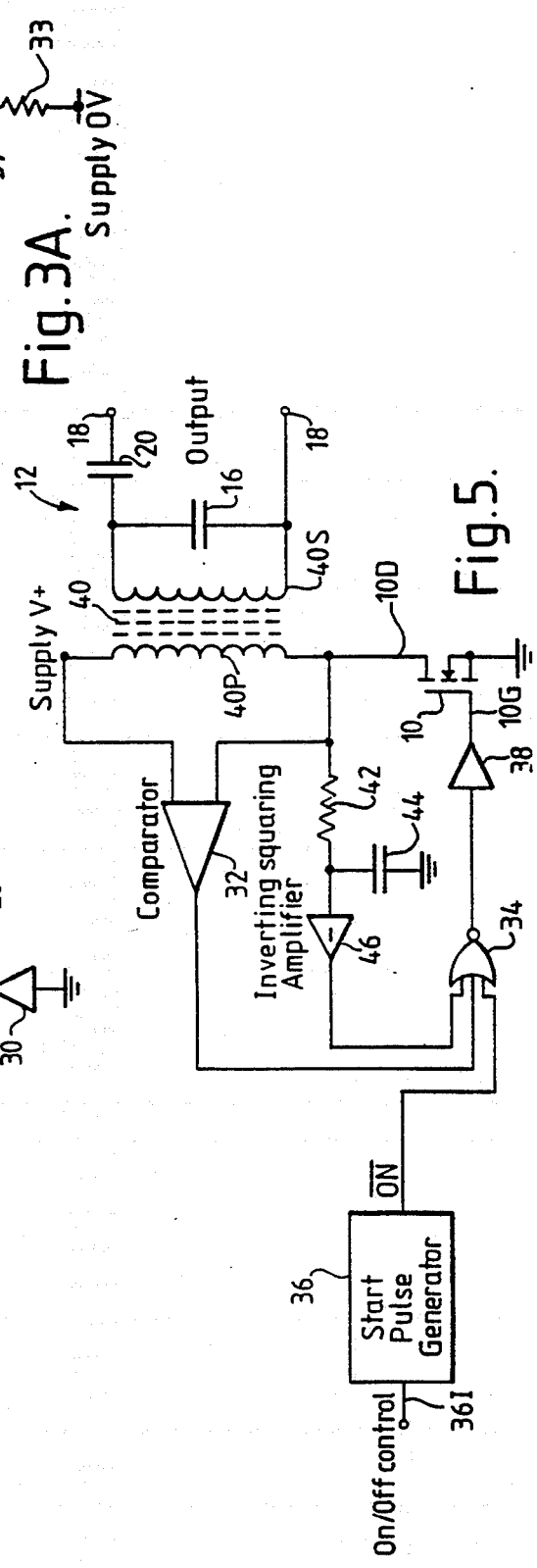

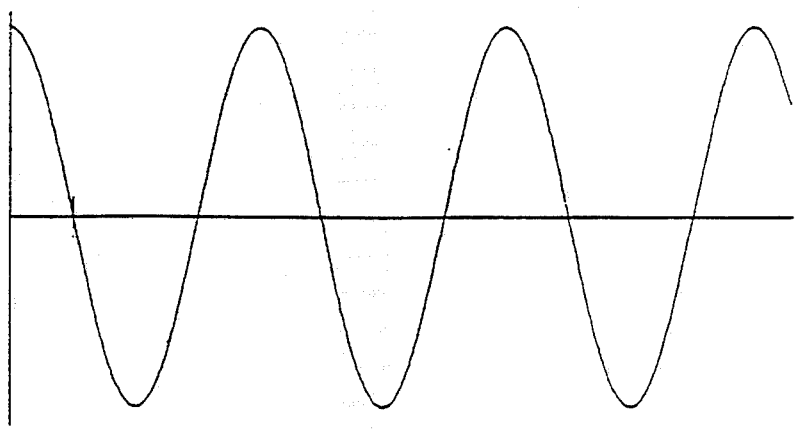
Output voltage
Fig.4A.
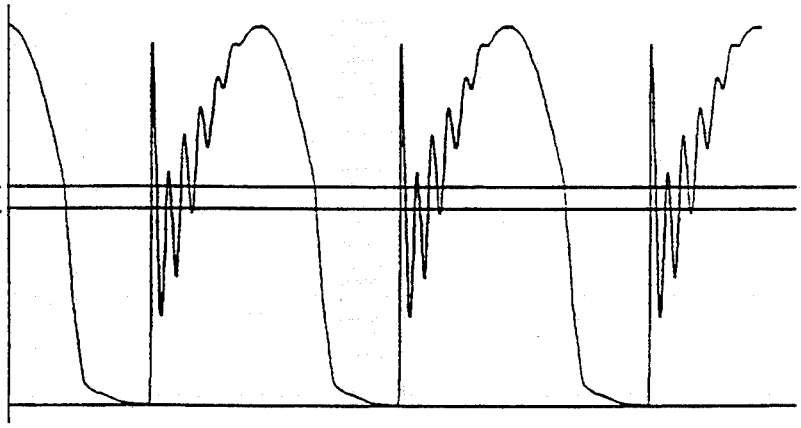
Primary voltage
'On' threshold →
Supply →
Fig.4B.
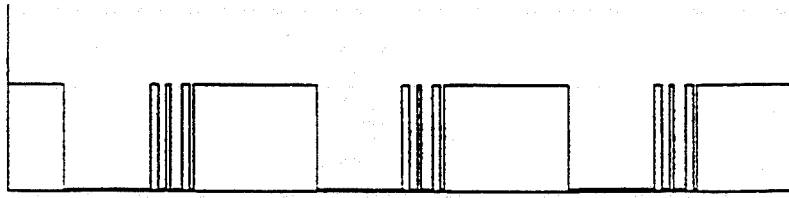
Voltage controlled 'on' signal
Fig.4C.
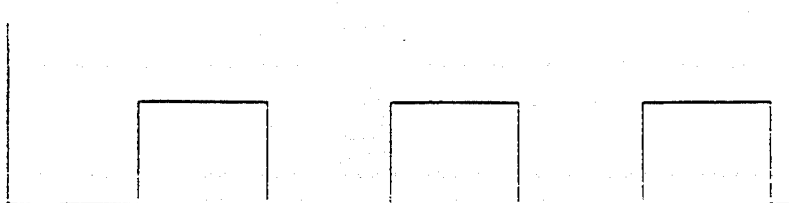
90° Phase Advance Derived from either primary or secondary
Fig.4D.
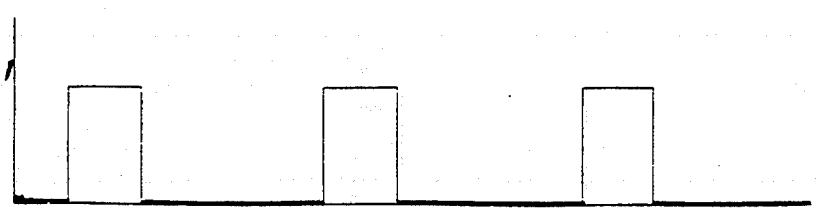
NORed Output and power switching control signal
Fig.4E.
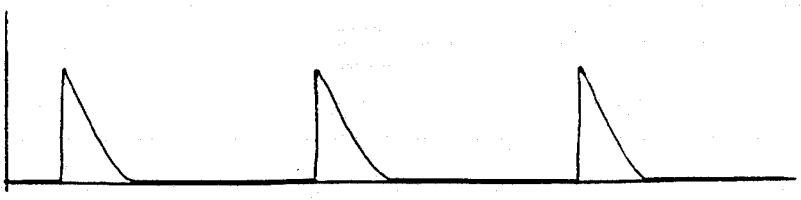
Fig.4F. $I_D$

ELECTROSURGICAL RADIOFREQUENCY GENERATOR HAVING REGULATED VOLTAGE ACROSS SWITCHING DEVICE

BACKGROUND OF THE INVENTION

This invention relates to an electrosurgical generator.

A radio frequency generator for electrosurgery conventionally has an output isolation transformer coupled to output terminals of the apparatus via a series coupling capacitor the function of which is to prevent low frequency output components causing nerve stimulation in the patient being treated. In electrosurgery, the impedance presented to the output terminals of the generator tends to vary widely, to the extent that the output stage is rarely matched, leading to reflection of power back into the output stage with consequently poor efficiency and unwanted heat dissipation. In this context "matched" means matching of the output impedance of the output stage to the load impedance, i.e. $Z_{out} = Z_{load}$. This effect may be overcome to a large degree by arranging for the output frequency to vary according to the magnitude of the load resistance, as described in published British Patent Application No. 2214430A, the disclosure of which is incorporated in this specification by reference. This prior apparatus has an output stage consisting of a self-tuning radio frequency oscillator having a power MOSFET driving a resonant output network coupled to the output terminals of the apparatus. The network consists of a transformer, the secondary winding of which is tuned by a parallel capacitor, and by a series coupling capacitor connected between one end of the winding and one of the terminals. It will be appreciated that the frequency of oscillation varies with load impedance, and reflection of power back into the generator can be maintained at relatively low levels over a wide range of load impedances. This is especially beneficial for a battery powered generator having a limited power output capacity. Stray capacitances resulting from connection of the generator to the load have little or no effect on matching. The prior disclosed apparatus does, however, have disadvantages. One of these is that under extreme load conditions, the only limit to the energy build up in the resonant output circuit is the Q of the circuit itself. If the generator is designed to produce a constant power output, for example, by pulsing the oscillator with a variable mark-to-space ratio according to sensed current drain and supply voltage, under extreme load conditions the oscillator energy at the required constant power is dissipated mainly by the resonant output circuit. Consequently, the output stage needs to be capable of dissipating the maximum design output power and the main oscillator device must be capable of withstanding the voltage levels necessary to achieve such power. Indeed, in bipolar electrosurgery the tissue impedance tends to be between 10Ω and 1KΩ, while in monopolar application it tends to be between 100Ω and 10KΩ. Since power, $P = V^2/R$ at resonance, the voltage applied to the output device can be $\sqrt{(PR)}$, P being the design power of the generator. In a low power generator (having a power output of 10 W typically), this may present no particular problems. However, for increased power outputs (for instance, up to 300 W) the resonant output circuit must be of heavy construction, and special measures must be taken to protect the output device.

Another difficulty concerns control of the oscillator device, specifically the feedback applied to a control terminal of the device to sustain oscillation. At higher power levels such control cannot be linear in the sense of operating the device as an amplifier so that the output current is proportional to the input voltage or input current, since the device must then dissipate a proportion of the oscillator power. The oscillator device is therefore preferably switched between the fully "on" and fully "off" conditions. Such switching brings the problem of higher harmonics being produced by the oscillator device, which are shunted by the resonant output circuit. This can, to some extent, be alleviated by switching the device 90° phase-advanced with respect to the resonant output waveform. Nevertheless, in an extreme load condition, which gives very high Q in the resonant output circuit, the 90° advance switching point causes the primary voltage to swing lower than the switching potential, assuming that the oscillator device is coupled between the transformer primary winding and ground. This occurs because the current injection immediately following the "on" instant is very high, the primary voltage at 90° advance usually being higher than the switching supply voltage. With constant power feedback control, this condition is also an unstable one, since as more energy is injected into the resonant output circuit, the primary voltage at the switching-on point becomes progressively higher and therefore the peak switching current also becomes higher. This can lead to reverse biasing of the oscillator device, leading to inefficiency and sometimes to damage of the device. When the device is a power MOSFET, this reverse current flow causes forward biasing of the intrinsic diode which, being a comparatively slow device, then dissipates a significant level of power at radio frequencies. Whilst the reverse bias performance can be improved by coupling an additional fast recovery diode in parallel with the intrinsic diode, any conduction as a result of the transformer primary voltage falling below the switching voltage is inefficient.

It is an object of this invention to provide a generator of improved efficiency.

SUMMARY OF THE INVENTION

According to this invention, an electrosurgical generator has a radio frequency oscillator comprising at least one switching device, a resonant output network coupled in series with the switching device in a path between power supply rails of opposite polarities, and an oscillator feedback circuit operable to feed to the switching device a switching control pulse signal as an oscillation feedback signal such that the switching device is cyclically switched to its "on" state whilst the voltage across the switching device is decreasing, the phase of the "on" point being automatically and dynamically variable such that the "on"-time of the switching device is adjusted. The oscillator feedback circuit is preferably operable to retard the "on" point at one or both extremes of the load impedance range of the generator, the phase of the "on" point being variably retarded so as to lag positive or negative peaks of the output signal voltage from the resonant output network by between 0° and 120°. By allowing the phase of the "on" point to be retarded when conditions require, the current surge that occurs when the switching device is switched to its "on" state is less severe due to the voltage across the switching device (generally the primary voltage of an output network transformer) being lower.

In this way, it is possible to limit the primary voltage amplitude so that reverse conduction of the switching device can be largely avoided.

The feedback circuit may be such that the "on" point is arranged to coincide with the voltage across the switching device falling to a predetermined threshold value which is equal to or greater than the potential difference between the supply rails of the power supply powering the switching device. The peak voltage across the switching device may exceed the supply voltage by a considerable margin and it is preferred that the threshold value is nearer to the supply voltage than the said peak voltage.

In the case of the resonant output network including a transformer having a primary winding coupled in series with the switching device, the feedback circuit may be arranged to produce a timing signal in response to the voltage across the primary winding crossing a predetermined threshold. Thus, the primary winding may have one end coupled to one of the supply rails, and the feedback circuit may include a comparator arranged to compare the voltage at the other end of the primary winding with a threshold voltage equal or approximately equal to the voltage of the said one supply rail.

Preferably, the feedback circuit is arranged such that the switching device is cyclically switched to its "off" state in the region of a positive or negative peak of the output signal voltage from the resonant network occurring between 0° and 180° after the switching to the "on" state. In this way, by retarding the phase of the switching "on" with respect to the "off" point, the "on" time of the switching device is reduced, leading to reduced input energy in the resonant output network under extreme load conditions. Thus, for a given output power rating, the power handling capability of the resonant output network can be reduced, as can the output voltage rating of the switching device.

In the preferred embodiment of the invention, the feedback circuit includes means coupled to the resonant output network for deriving a phase-shifted pulse signal having a pulse edge in the region of the above-mentioned positive or negative output signal voltage peak. These deriving means are associated with a logic circuit having one input coupled to the output of the deriving means to receive the phase-shifted pulse signal and another input coupled to an output of the comparator to produce the switching control pulse signal with pulses each of which begins when the comparator indicates that the voltage across the primary winding equals the threshold voltage, and ends at the said pulse edge of the phase-shifted pulse signal. The deriving means may comprise a capacitive filter and a squaring circuit which are operable together to produce a pulse signal as a squared representation of the output signal voltage from the resonant network, shifted by approximately 90°. The logic circuit preferably produces an "on" signal when both of the said inputs are in the same, predetermined logic condition.

To aid starting of the oscillator, the comparator may be biased such that when the switching device is in its "off" state and the oscillator quiescent, the comparator output is in a logic state which, in the presence of a start signal, causes the switching device to be switched to its "on" state. The logic circuit may have a third input coupled to receive the start signal.

The resonant network may include an auto-transformer having a primary winding coupled between the switching device and the supply rail and/or an AC earth, and a secondary winding coupled to an output terminal of the oscillator. In this case, the feedback circuit preferably includes a feedback link with a series-connected capacitor coupled to the secondary winding for deriving a phase-shifted signal representative of the output signal voltage phase-shifted by approximately 90°.

Alternatively, for mains powered use, the resonant network may include a transformer having a primary winding coupled between the switching device and a supply rail and/or an AC earth, and a secondary winding DC-isolated from the primary winding and coupled to an output terminal of the oscillator. In this latter case, the feedback circuit preferably includes a feedback link comprising an RC network having a series resistance and a downstream parallel capacitance, and a squaring circuit which, together with the RC network, is operable to produce a phase-shifted signal representative of the output signal phase-shifted by 90°, the feedback link being coupled to the primary winding.

For simplicity, and for rapid response to the rapid changes in impedance which typically arise in electrosurgery, the oscillator is preferably self-tuning, in that the resonant network comprises a transformer having a primary winding coupled between the switching device and a supply rail and/or AC earth, and a secondary winding, a first tuning capacitance coupled across the secondary winding, and second coupling capacitance coupled to one end of the second winding for connection to the load. Thus, when the oscillator is connected to the load, the frequency of oscillation varies automatically according to the impedance of the load in order to maintain a substantial impedance match over a range of load impedance values. In order maintain a substantially constant output over a range of load impedances, the oscillator may include a power control circuit for pulsing the oscillator at a pulse repetition rate which is much lower than the frequency of oscillation, the pulse duty cycle being varied to maintain the output of the oscillator substantially constant. The power control circuit may comprise means for monitoring the current drawn from the supply rails by the oscillator and the supply rail voltage, a multiplier coupled to the monitoring means for deriving a product signal representative of output power, and a circuit arrangement for altering the pulse duty cycle according to the value of the product signal.

The generator may be monopolar or bipolar. A bipolar generator has a pair of output terminals for connection to an electrosurgical or diathermy load, the terminals preferably being coupled to opposite ends of the secondary winding of the transformer, with at least one of the terminals being coupled via a series coupling capacitor to achieve matching with varying load impedance as mentioned above.

BRIEF DESCRIPTION OF THE DRAWINGS

FIG. 3 is a circuit diagram of a first self-tuning oscillator of an electrosurgical generator in accordance with the invention;

FIG. 3A is a block diagram showing a power control circuit;

FIGS. 4A to 4F are waveform diagrams relating to the oscillator of FIG. 3; and

FIG. 5 is a further self-tuning oscillator.

DETAILED DESCRIPTION OF THE PREFERRED EMBODIMENTS

Figure 1:
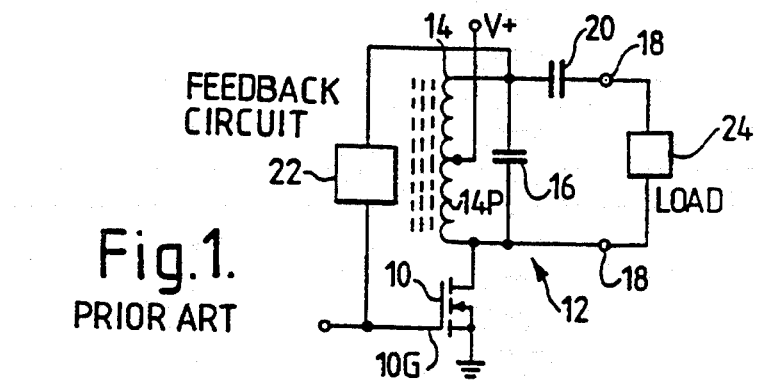
FIG. 1 is a circuit diagram of a self-tuning oscillator of an electrosurgical generator.

Referring to FIG. 1, a prior art electrosurgical generator has a self-tuning oscillator with a MOSFET oscillator device 10 coupled in series with a resonant output network 12 between a positive voltage supply rail V+ and earth. The resonant network 12 has an inductor configured as an autotransformer 14 with a parallel tuning capacitance 16 coupled across the complete winding and a pair of output terminals 18, one of which is isolated from the transformer 14 and parallel capacitor 16 by a series coupling capacitor 20. One portion of the transformer secondary winding acts as a primary winding 14P which is coupled between the supply V+ and the drain terminal of the MOSFET 10. A feedback circuit 22 links one end of the secondary winding to a gate terminal 10G of the MOSFET 10. A generator having such an oscillator is described in more detail in the above-mentioned British Patent Application No. 2214430A. It will be noted that this particular oscillator has two output terminals 18, representing the outputs of a bipolar electrosurgical generator which, in use, are connected to an electrosurgical load 24.

It is well known that the load presented to an electrosurgical generator varies widely and very rapidly according to the particular operation being performed and, for example, the movements of the electrosurgical instrument with respect to the tissue being treated. As described in the above-mentioned patent, a resonant network such as that shown in FIG. 1, having both a parallel tuning capacitor across the transformer secondary and a series coupling capacitor allows the oscillator to be matched to the load as the load impedance varies.

Figure 2A:
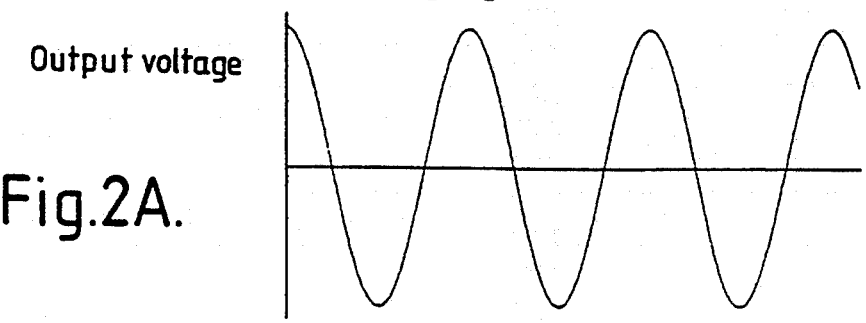
FIGS. 2A to 2D are waveform diagrams relating to an oscillator in which the oscillating device is driven by a square wave control signal.
Figure 2B:
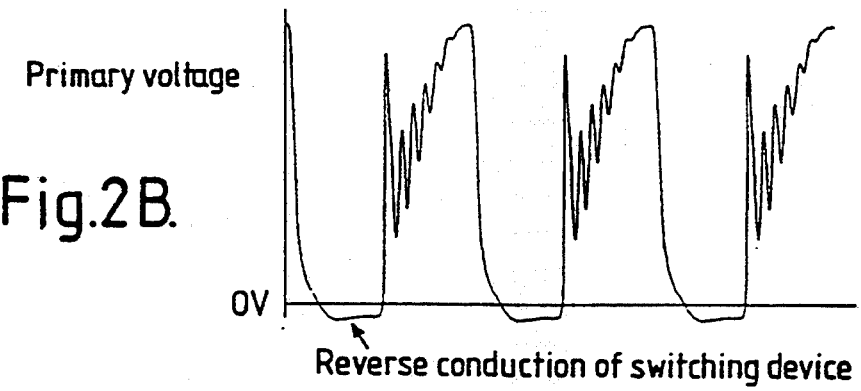
Figure 2C:
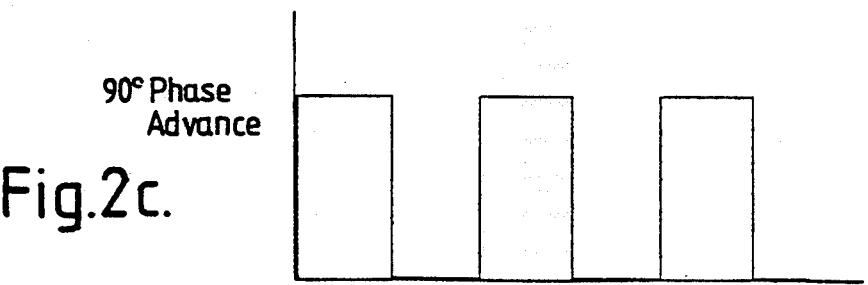
Figure 2D:
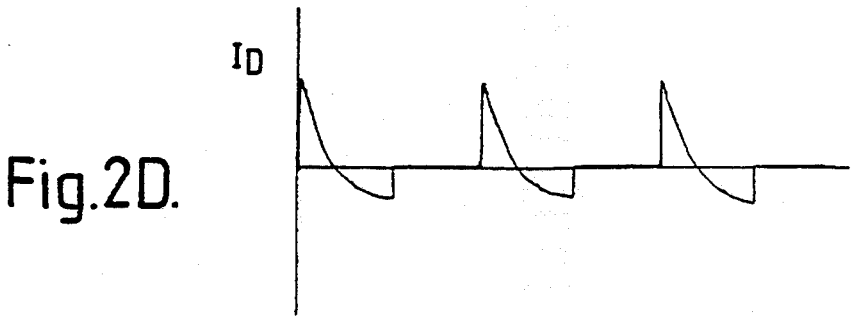

Conventionally, the feedback circuit 22 is a capacitor. If the feedback voltage applied to the gate terminal 10G of the MOSFET 10 is squared so that the MOSFET is driven between the fully "on" and fully "off" states in order largely to avoid power dissipation in the MOSFET 10, the signals at different points in the oscillator circuit have the form shown in FIGS. 2A to 2C. The waveform of FIG. 2A represents the output voltage across the secondary winding. In this diagram, the mean voltage is shown by a horizontal line. The primary voltage waveform for infinite load impedance is shown in FIG. 2B. This has a non-sinusoidal shape by virtue of the square wave drive to the MOSFET gate 10G, as shown by the waveform of FIG. 2C. The drive waveform is, in effect, advanced by 90° with respect to the output voltage so that the MOSFET is switched to its "on" state 90° before the zero-crossing of the output voltage waveform (zero-crossing meaning here the crossing of the mean voltage line) so that current is drawn from the resonant network through the MOSFET before the corresponding voltage peak (a negative peak in FIG. 2A). At the 90° phase-advanced switch point the primary voltage on the drain terminal of MOSFET 10 may be higher than the supply voltage V+ when the load impedance is high, with the result that the current injection occurring immediately after the "on" time is very high. It is this current injection which causes the primary voltage, as shown in FIG. 2B to change very rapidly and, in certain conditions to swing lower than the switching potential on the MOSFET (which here switches to ground), producing reverse conduction through the MOSFET. This effect is visible in FIG. 2B as negative pulses below the zero voltage line. The MOSFET current $I_D$ is shown in FIG. 2D. As has been described above, this is an undesirable condition, leading to inefficiency and potentially to damage of the MOSFET 10.

As will be seen from FIG. 2C, the "off" point of the control signal applied to the gate terminal of the MOSFET 10 corresponds approximately to the instant of the peak of the output voltage waveform following switching on and is, therefore, 90° phase-advanced with respect to the corresponding part of the output voltage waveform.

An improved generator in accordance with the invention is illustrated in FIG. 3. Like the generator of FIG. 1, this is intended to be used primarily as a battery powered generator. In common with the oscillator of FIG. 1 a MOSFET 10, the oscillator has a resonant output network 12 comprising a transformer 14, a parallel capacitor 16, and a series coupling capacitor 20. Bipolar output terminals 18 are provided for connection to an electrosurgical instrument. The transformer 14 is an auto transformer, the output for application to the electrosurgical instrument being developed across the secondary winding represented by the full winding of the transformer 14, the primary winding being represented by part of the full winding, in this case the upper portion of the winding as shown in FIG. 3, with the tap 14T being connected to the drain terminal 10D of the MOSFET 10.

The feedback circuit of this improved oscillator is arranged in two parts. The first part comprises a feedback link having a series connected feedback capacitor 26 the output side of which is clamped between +5V and earth by diodes 28, 30 to provide a squared 90° phase-advanced signal similar to that shown in FIG. 2C, but inverted. The other part of the feedback circuit comprises a comparator 32 having a first input coupled to the junction of the transformer 14 and the drain terminal of the MOSFET 10 which carries the transformer primary voltage, and a second input coupled to the supply rail V+. The comparator thus compares the primary voltage with a threshold voltage equal to the supply voltage to produce a square wave at its output which is presented to one input of a NOR gate 34, another input of which is coupled to the clamped output side of the feedback capacitor 26. NOR gate 34 has a third input which, when the oscillator is active is held low by a start pulse generator 36 having an on/off control input 36I. It will be seen that all three inputs of the NOR gate 34 must be driven low for the output to be positive. Otherwise the output is negative. This NOR gate 34 provides a pulsed control signal via a buffer amplifier 38 for the gate 10G of the MOSFET 10. The polarities of the signals obtained from the comparator 32 and the clamped output of the capacitor 26 are such that a positive drive pulse is provided to the MOSFET 10 only when the primary voltage is lower than the voltage threshold (here the battery supply voltage V+) and the 90° signal from the capacitor 26 indicates that the output voltage from the resonant output network 12 is falling from a positive peak to a negative peak.

The result of these measures is shown in the waveform diagrams of FIGS. 4A to 4E. The output voltage across the secondary winding of the transformer 14 is shown in FIG. 4A and is a sinusoid of a frequency equal to the resonant frequency of the network 12. The primary voltage is shown in FIG. 4B, this being the voltage at the junction between the MOSFET drain connection 10D and the transformer 14, while the output from the comparator 32 resulting from the comparison of this primary voltage with a threshold voltage approximately equal to the supply voltage V+ is a pulsed signal as shown in FIG. 4C. (It should be noted here that the threshold voltage in FIG. 4B is a little higher than the supply voltage, since in one preferred embodiment of the invention, potential dividers connected between the supply V+ and the comparator on the one hand and between the primary voltage connection and the comparator on the other hand are arranged to select a somewhat higher threshold. This also has the effect of biasing the comparator output to the negative state in order that the oscillator may be started when a negative-going start pulse is produced by the start pulse generator 36.)

The 90° phase advanced signal produced at the clamped output of the capacitor 26 is shown in FIG. 4D, from which it will be seen that the phase-advanced signal is a simple square wave 90° phase-advanced with respect of the output voltage of FIG. 4A. Providing the output of the start pulse generator 36 is low, the control signal obtained from the output of the NOR gate 34 takes the form shown in FIG. 4E, i.e. positive pulses coinciding with the incidence of low input states from both the comparator 32 and the capacitor 26. The result is that the MOSFET 10 is switched on cyclically at an instant which is retarded with respect to the 90° advanced point but is still switched "off" in the region of the first peak of the output voltage following switch on (i.e. in the region of a null of the differential dv/dt of the output voltage).

Referring now to FIG. 4B, it will be seen that, since the primary voltage is lower when the MOSFET 10 is switched "on" than with the switching scheme of FIG. 2C, the primary voltage in the no-load condition does not cross below the switching potential represented by the base line of the diagram in FIG. 4B, nor does the device current $I_D$ exhibit reversals (see FIG. 4F). Consequently, inefficient and potentially damaging reverse conduction is avoided. Furthermore, since the "on" point is retarded, but the "off" point remains substantially coincident with the output voltage peak, the total "on" time of the MOSFET is reduced with respect to the arrangement represented by the waveform diagrams FIGS. 2B and 2C, leading to reduced power consumption at the extremes of load impedance, thereby avoiding excessive power dissipation in the resonant output network. Since the triggering of the MOSFET 10 is dependent on the amplitude and shape of the primary voltage waveform, the "on" duration of the MOSFET varies according to the load impedance appearing at the output terminals 18 (see FIG. 3). It has been found that use of this switching arrangement results in very high energy conversion efficiencies over relatively large load impedance ranges. In practice, it is possible to achieve greater than 70% efficiency for maximum power over a load impedance range of 10Ω to 1000Ω, representing a tenfold change in both current and voltage output.

A power control feedback loop may be included, operable to pulse the MOSFET oscillator by applying a relatively low frequency pulsed control input to the start pulse generator 36. Details of a suitable power control circuit are shown in the above-mentioned British Patent Application No. 2214430A.

The circuit is shown in simplified form in FIG. 3A. In FIG. 3A, the circuitry of FIG. 3 is shown as oscillator 31. Current for the oscillator 31 is drawn from the supply rails V+ and OV through a shunt-connected current-monitoring resistor 33, the voltage across this resistor 33 being fed together with the supply voltage V+ to a multiplier 35. The multiplier output is connected to a comparator 37 which receives from the multiplier 35 a product signal representative of the output power of the oscillator and compares it with a reference voltage $V_{REF}$ to produce the low frequency pulsed control input to the input 36I of the start pulse generator 36 (see FIG. 3).

With such a control circuit, the enhanced conversion efficiency yielded by the circuitry of the invention allows the load impedance/power characteristic to be tailored flat over an extended load impedance range without excessive resonant circuit dissipation or excessive stress on the switching MOSFET 10, the variable phase-advance switching limiting the maximum output voltage (no-load condition) and maximum current (short circuit load). These advantages give rise to reduced power supply requirements and the possibility of cheaper components for a given required power output.

The circuitry of FIG. 3 is intended for battery supplied electrosurgical apparatus. Where the apparatus is mains supplied, additional isolation is required, preferably in the form of an output RF transformer with an isolated secondary, as shown in FIG. 5. As before, the primary winding is coupled between the supply V+ and the drain terminal 10D of a MOSFET 10. The isolated secondary winding 40S of the transformer 40 is coupled to the output terminals 18 in the same way as the secondary portion of the auto transformer 14 of the oscillator of FIG. 3.

Whereas in the oscillator of FIG. 3 it is possible to use a feedback signal directly from the output stage due to the absence of a need for d.c. isolation, the mains driven oscillator requires alternative means for generating the 90° phase-advanced signal. In this case, then, in the oscillator of FIG. 5 the feedback circuit includes a single pole low pass filter comprising RC network 42, 44 connected to receive the primary voltage available at the junction of the primary winding 40P and the drain terminal 10D of the MOSFET 10, followed by an inverted 46. This actually produces a delayed 90° signal but does not affect the operation of the MOSFET. A comparator 32 is arranged to compare the primary voltage with the supply voltage V+ or, preferably, a voltage slightly higher.

At this point it should be mentioned that the delayed 90° phase-advanced signal produced by the low pass filter and squaring inverter arrangement 42, 44, 46 would, on its own, not allow the oscillator to start when power is first applied, since no 90° phase-advanced signal is available for the first cycle of oscillation. This difficulty is overcome by the start pulse generator 36 being arranged to produce a negative pulse. In fact, the pulse start duration is relatively short (typically 50–100 ns). In both circuits, (i.e. the oscillators of FIG. 3 and FIG. 5) the short duration of this pulse limits the initial current surge so that the possibility of damage to the MOSFET 10 is reduced. Subsequently, excessive current is avoided by the retarded "on" instant as described above.

The embodiments of FIGS. 3 and 5 both include single-sided switch arrangement in that current through the primary winding of the transformer 14 or 40 is controlled by switching means 10 on one side only of the winding. It should be mentioned that the invention includes within its scope a push-pull arrangement which would be advantageous at high power levels because the resulting balancing-out of DC current components allows a smaller transformer core to be used for a given power rating by virtue of the raising of the effective transformer core saturation point.

The oscillator operates within the range 200 kHz to 2 MHz. The preferred frequency of operation at the middle of the load range is typically in the region of 500 kHz.

What is claimed is:

1. An electrosurgical generator having a radio frequency oscillator comprising at least one switching device, a resonant output network coupled in series with the switching device in a path between power supply rails of opposite polarities, and an oscillator feedback circuit operable to feed to the switching device a switching control pulse signal as an oscillation feedback signal such that the switching device is cyclically switched to its "on" state whilst the voltage across the switching device is decreasing, the phase of the "on" point being dynamically variable such that the "on"-time of the switching device is adjusted to regulate the amplitude of the voltage across the switching device.

2. A generator according to claim 1, wherein the oscillator feedback circuit is operable to retard the "on" point at at least one extreme of a load impedance range of the generator.

3. A generator according to claim 1, wherein the phase of the "on" point is retarded so as to lag a positive or negative peak of the output signal voltage from the resonant output network by values between 0° and 120°.

4. A generator according to claim 1, wherein the feedback circuit is operable such that the "on" point coincides with the existence of a predetermined instantaneous voltage value across the switching device.

5. A generator according to claim 4, wherein the predetermined voltage value is at least as great as the potential difference between the supply rails of the oscillator.

6. A generator according to claim 5, wherein the predetermined voltage value is greater than the potential difference between the supply rails of the oscillator but closer to the said potential difference than to the peak instantaneous voltage value across the switching device.

7. A generator according to any of claims 1 to 3, wherein the resonant output network includes a transformer having a primary winding coupled in series with the switching device, and wherein the feedback circuit is operable to produce a timing signal in response to the voltage across the primary winding crossing a predetermined threshold.

8. A generator according to claim 7, wherein the primary winding has one end coupled to one of the supply rails, and the feedback circuit includes a comparator arranged to compare the voltage at the other end of the primary winding with a threshold voltage at least approximately equal to the voltage of the said one supply rail.

9. A generator according to claim 1, wherein the feedback circuit is operable such that the switching device is cyclically switched to its "off" state in the region of a positive or negative peak of the output signal voltage from the resonant network occurring between 0° and 180° after the switching to the "on" state.

10. A generator according to claim 8, wherein the feedback circuit includes means coupled to the resonant network for deriving a phase-signal pulse signal having a pulse edge in the region of the said positive or negative peak, and a logic circuit having one input coupled to the deriving means to receive the phase-shifted pulse signal and another input coupled to an output of the comparator to produce the switching control pulse signal with pulses each beginning when the comparator indicates that the voltage across the primary winding equals the threshold voltage and ending at the said pulse edge of the phase-shifted pulse signal.

11. A generator according to claim 10, wherein the deriving means comprises a capacitive filter and a squaring circuit operable together to produce a pulse signal which is a squared representation of the output signal voltage from the resonant network shifted by approximately 90°, and wherein the logic circuit produces an "on" signal when both of the said inputs are in the same, predetermined logic condition.

12. A generator according to claim 8, wherein the comparator is biased such that when the switching device is in its "off" state and the oscillator is quiescent, the comparator output is in a logic state which, in the presence of a start signal, causes the switching device to be switched to its "on" state.

13. A generator according to claim 12, wherein the logic circuit has a third input coupled to receive the start signal.

14. A generator according to claim 1, wherein the resonant network includes an auto-transformer having a primary winding coupled between the switching device and a supply rail and/or an a.c. earth, and a secondary winding coupled to an output terminal of the oscillator.

15. A generator according to claim 14, wherein the feedback circuit includes a feedback link with a series connected capacitor coupled to the secondary winding for deriving a phase-shifted signal representative of the output signal voltage phase-shifted by approximately 90°.

16. A generator according to claim 1, wherein the resonant network includes a transformer having a primary winding coupled between the switching device and a supply rail and/or an a.c. earth, and a secondary winding d.c. isolated from the primary winding and coupled to an output terminal of the oscillator.

17. A generator according to claim 16, wherein the feedback circuit includes a feedback link comprising an RC network having a series resistance and a downstream parallel capacitance, and a squaring circuit which, together with the RC network, is operable to produce a phase-shifted signal representative of the output voltage signal phase shifted by 90°, the feedback link being coupled to the primary winding.

18. An electrosurgical generator according to claim 1, wherein the oscillator is self-tuning and the resonant network comprises
a transformer having a primary winding coupled between the switching device and a supply rail and/or a.c. earth, and a secondary winding,
a first, tuning, capacitance coupled across the secondary winding, and
a second, coupling, capacitance coupled to one end of the secondary winding for connection to a load,
whereby when the oscillator is connected to the load the frequency of oscillation of the oscillator varies automatically according to the impedance of the load in order to maintain a substantial impedance match over a range of load impedance values.

19. A generator according to claim 18, including a power control circuit for pulsing the oscillator at a pulse repetition rate which is much lower than the frequency of oscillation, the pulse duty cycle being varied to maintain the output power of the oscillator substantially constant over a range of load impedance values.

20. A generator according to claim 19, including means for monitoring the current drawn from the supply rails by the oscillator and the supply rail voltage, a multiplier coupled to said monitoring means for deriving a product signal representative of the output power, and a circuit arrangement for altering the said pulse duty cycle according to the value of the product signal.

21. A generator according to claim 18, having a pair of output terminals for connection to an electrosurgical load, the terminals being coupled to opposite ends of the secondary winding of the transformer, at least one of the terminals being so coupled via a series coupling capacitor.

* * * * *

UNITED STATES PATENT AND TRADEMARK OFFICE
CERTIFICATE OF CORRECTION

PATENT NO.    : 5,438,302

DATED         : August 1, 1995

INVENTOR(S)   : Colin Charles Owen Goble

It is certified that error appears in the above-identified patent and that said Letters Patent is hereby corrected as shown below:

On the title page, item [75], "Penarth, Scotland" should be --S. Glamorgan, Wales, United Kingdom--.

Col. 1, line 63, "10 W" should be --10W--.

Col. 1, line 65, "300 W" should be --300W--.

Col. 7, line 41, "$I_O$" should be --$I_D$--.

Signed and Sealed this

Seventeenth Day of September, 1996

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO.   : 5,438,302

DATED        : August 1, 1995

INVENTOR(S)  : Colin Charles Owen Goble

It is certified that error appears in the above-identified patent and that said Letters Patent is hereby corrected as shown below:

Col. 10, line 5 change "phase-signal" to --phase-shifted--.

Signed and Sealed this

Twenty-ninth Day of October 1996

*Attest:*

BRUCE LEHMAN

*Attesting Officer*      *Commissioner of Patents and Trademarks*